United States Patent
Laurence et al.

(10) Patent No.: US 12,162,649 B2
(45) Date of Patent: Dec. 10, 2024

(54) CONTAINMENT AND DELIVERY SYSTEMS FOR CRYOGENIC STORAGE

(71) Applicant: West Pharmaceutical Services, Inc., Exton, PA (US)

(72) Inventors: Lawton E. Laurence, Chester Springs, PA (US); Alex Lyness, West Chester, PA (US); Geoffrey T. Rouin, Morristown, NJ (US); Christopher Evans, Long Valley, NJ (US)

(73) Assignee: West Pharmaceutical Services, Inc., Exton, PA (US)

( * ) Notice: Subject to any disclaimer, the term of this patent is extended or adjusted under 35 U.S.C. 154(b) by 0 days.

(21) Appl. No.: 17/799,608

(22) PCT Filed: Feb. 8, 2021

(86) PCT No.: PCT/US2021/017065
§ 371 (c)(1),
(2) Date: Aug. 12, 2022

(87) PCT Pub. No.: WO2021/162984
PCT Pub. Date: Aug. 19, 2021

(65) Prior Publication Data
US 2023/0064423 A1     Mar. 2, 2023

Related U.S. Application Data

(60) Provisional application No. 62/975,878, filed on Feb. 13, 2020.

(51) Int. Cl.
*B65D 39/12*     (2006.01)
*A61J 1/14*      (2023.01)
(Continued)

(52) U.S. Cl.
CPC ............ *B65D 39/12* (2013.01); *A61J 1/1412* (2013.01); *A61M 5/31513* (2013.01);
(Continued)

(58) Field of Classification Search
CPC ...... A61J 1/1412; A61J 1/1468; A61J 1/1406; A61M 5/31513; B65D 39/12; F16J 15/32;
(Continued)

(56) References Cited

U.S. PATENT DOCUMENTS 730,720 A * 6/1903 Thomas ............ A61M 5/31513
                                              604/219
829,546 A * 8/1906 Schou ....................... F16J 15/22
                                              277/538
(Continued)

FOREIGN PATENT DOCUMENTS

CN        1526610 A        9/2004
CN      101001782 A        7/2007
(Continued)

OTHER PUBLICATIONS

Dictionary definition "Flexible" https://www.merriam-webster.com/dictionary/flexible (Year: 2024).*
(Continued)

*Primary Examiner* — Gideon R Weinerth
(74) *Attorney, Agent, or Firm* — Blank Rome LLP

(57) ABSTRACT

Various systems for the containment or delivery of a product are provided. The systems allow for the storage of products at low temperatures and include a container closure inserted into a container (10). The container closure may have an elastomeric body (12) and include a material (14) having a negative coefficient of thermal expansion. In other systems, the material having a negative coefficient of thermal expansion may be inserted between the elastomeric container closure and a seal. Other systems may include an insert at (Continued)

least partially embedded within the elastomeric body of a container closure, an actuator having a distal end movably attached to the insert, and a resilient element between the distal end of the actuator and the insert, wherein the resilient material expands radially upon displacing the distal end of the actuator toward the insert.

22 Claims, 11 Drawing Sheets

(51) Int. Cl.
    *A61M 5/315*          (2006.01)
    *F16J 15/32*           (2016.01)
    *B01L 3/00*            (2006.01)
    *F16J 15/16*           (2006.01)

(52) U.S. Cl.
    CPC .......... *B01L 3/5085* (2013.01); *F16J 15/164* (2013.01); *F16J 15/32* (2013.01)

(58) Field of Classification Search
    CPC .......... F16J 15/164; F16J 15/068; F16J 15/46; F16J 15/022; B01L 3/50825; B01L 2300/042; B01L 2300/123; Y10S 285/91; Y10S 285/918; Y10S 285/904
    USPC .......... 215/246, 355–364; 220/233
    See application file for complete search history.

(56) References Cited

U.S. PATENT DOCUMENTS

| | | | | |
|---|---|---|---|---|
| 1,966,202 A * | 7/1934 | Pfefferle | ............... | F16L 21/04 165/178 |
| 2,592,381 A * | 4/1952 | Blackman | ............ | A61M 5/31511 604/222 |
| 2,914,350 A * | 11/1959 | Smith | ............... | F16L 23/18 277/645 |
| 3,007,600 A * | 11/1961 | Horner | ............... | F16J 15/46 220/240 |
| 3,149,848 A * | 9/1964 | Galloway | ............ | F16J 15/32 277/584 |
| 3,156,373 A * | 11/1964 | Willis | ............... | F41A 17/44 220/237 |
| 3,630,533 A * | 12/1971 | Butler | ............... | F17C 13/00 285/354 |
| 3,747,479 A * | 7/1973 | Nightingale | ........... | F16J 15/32 604/219 |
| 3,834,387 A * | 9/1974 | Brown | ............ | A61M 5/31513 604/125 |
| 4,757,911 A | 7/1988 | Larkin et al. | | |
| 4,865,331 A * | 9/1989 | Porter | ............... | H01L 23/445 277/637 |
| 5,279,606 A * | 1/1994 | Haber | ............... | A61J 1/2093 215/364 |
| 5,294,133 A * | 3/1994 | Dutta | ............... | F16J 15/32 277/910 |
| 5,487,490 A | 1/1996 | Estes | | |
| 5,549,573 A * | 8/1996 | Waskonig | ........ | A61M 5/31513 604/230 |
| 5,620,187 A * | 4/1997 | Jia | ............... | F16J 15/0887 285/341 |
| 5,919,720 A * | 7/1999 | Sleight | ............... | C04B 35/495 501/153 |
| 5,921,419 A * | 7/1999 | Niedospial, Jr. | ..... | B65D 51/002 215/247 |
| 6,004,300 A * | 12/1999 | Butcher | ............ | B29C 45/1675 604/218 |
| 6,695,829 B2 | 2/2004 | Hellstrom | ............ | A61J 1/2096 604/905 |
| 7,111,848 B2 * | 9/2006 | Tachikawa | ............ | B29C 43/021 604/230 |
| 7,417,315 B2 * | 8/2008 | Hougham | ............ | B81B 3/0035 257/E23.128 |
| 7,749,202 B2 * | 7/2010 | Miller | ............... | A61M 5/31511 604/218 |
| 10,258,744 B2 * | 4/2019 | Laubach | ............ | A61M 5/31513 |
| 10,280,086 B2 * | 5/2019 | Fukazawa | ............ | C04B 22/008 |
| 10,465,796 B2 * | 11/2019 | Sander | ............... | F16J 15/022 |
| 2002/0023409 A1 * | 2/2002 | Py | ............... | B65D 39/007 53/426 |
| 2003/0088216 A1 * | 5/2003 | Py | ............... | A61M 5/3129 604/203 |
| 2003/0233075 A1 * | 12/2003 | Huegli | ............... | A61M 5/486 604/222 |
| 2005/0191515 A1 * | 9/2005 | Brese | ............... | C04B 35/495 428/632 |
| 2005/0205686 A1 | 9/2005 | Yildirim et al. | | |
| 2007/0246156 A1 * | 10/2007 | Kohlmann | ............ | C03C 27/10 428/44 |
| 2007/0246468 A1 * | 10/2007 | Miller | ............... | F16L 55/1141 220/802 |
| 2010/0236659 A1 * | 9/2010 | Py | ............... | B65B 3/003 141/69 |
| 2014/0054291 A1 * | 2/2014 | Lewis | ............... | B65D 51/12 264/250 |
| 2014/0142500 A1 | 5/2014 | Newell et al. | | |
| 2014/0144911 A1 * | 5/2014 | Carlson | ............... | B65B 7/2842 53/485 |
| 2014/0249483 A1 * | 9/2014 | Kiilerich | ............ | A61M 5/31501 604/220 |
| 2015/0014321 A1 | 1/2015 | Chiang et al. | | |
| 2015/0166223 A1 * | 6/2015 | Yamamoto | ......... | B65D 39/0052 215/364 |
| 2015/0198248 A1 * | 7/2015 | Kiilerich | ............ | A61M 5/24 92/172 |
| 2016/0022917 A1 * | 1/2016 | Takai | ............... | A61M 5/31513 604/222 |
| 2016/0068728 A1 * | 3/2016 | Akulichev | ........... | C09K 3/1025 524/424 |
| 2017/0368264 A1 * | 12/2017 | Fournier | ............... | A61L 31/049 |
| 2019/0054246 A1 | 2/2019 | Ganton et al. | | |
| 2019/0375655 A1 * | 12/2019 | Takenaka | ............ | C01G 49/009 |
| 2020/0338272 A1 * | 10/2020 | Yotsutsuji | ......... | A61M 5/31515 |
| 2021/0085856 A1 * | 3/2021 | Ding | ............... | A61M 5/148 |
| 2021/0212893 A1 * | 7/2021 | Christie | ............... | B65D 1/023 |
| 2022/0168185 A1 * | 6/2022 | Redkar | ............... | A61J 1/1412 |
| 2022/0339067 A1 * | 10/2022 | Christie | ............... | B65B 3/003 |
| 2023/0064423 A1 * | 3/2023 | Laurence | ............... | B65D 39/12 |
| 2023/0088243 A1 * | 3/2023 | Tanaka | ............... | A61F 9/0008 222/420 |
| 2023/0144783 A1 * | 5/2023 | Christie | ............... | A61J 1/1412 604/403 |
| 2023/0145765 A1 * | 5/2023 | McNamara | ............ | B65D 55/10 215/340 |
| 2023/0157927 A1 * | 5/2023 | Christie | ............... | A61J 1/065 53/471 |
| 2023/0233407 A1 * | 7/2023 | Christie | ............... | B65D 1/023 428/34.4 |
| 2023/0270935 A1 * | 8/2023 | Lyness | ............... | A61M 5/283 604/232 |
| 2023/0347063 A1 * | 11/2023 | Moser | ............... | A61M 5/31501 |

FOREIGN PATENT DOCUMENTS

| | | | |
|---|---|---|---|
| CN | 110375067 A | | 10/2019 |
| CN | 110719836 A | | 1/2020 |
| CN | 115180297 A | * | 10/2022 |
| DE | 11 44 143 B | | 2/1963 |
| GB | 1 276 485 A | | 6/1972 |
| JP | 2016534810 A | | 11/2016 |
| WO | WO 94/03743 | * | 2/1994 ............... F16J 15/16 |
| WO | 2004026695 A2 | | 4/2004 |
| WO | WO 2009/087141 A1 | | 7/2009 |
| WO | 2015065942 A1 | | 5/2015 |
| WO | 2017082643 A1 | | 5/2017 |
| WO | 2018226780 A1 | | 12/2018 |

(56) References Cited

FOREIGN PATENT DOCUMENTS

| WO | 2019115974 A1 | 6/2019 |
|----|---------------|--------|
| WO | 2020259494 A1 | 12/2020 |

OTHER PUBLICATIONS

Dictionary definition "Elastic" https://www.merriam-webster.com/dictionary/elastic (Year: 2024).*
International Search Report and Written Opinion from PCT/US2021/017065 dated Jun. 16, 2021.

* cited by examiner

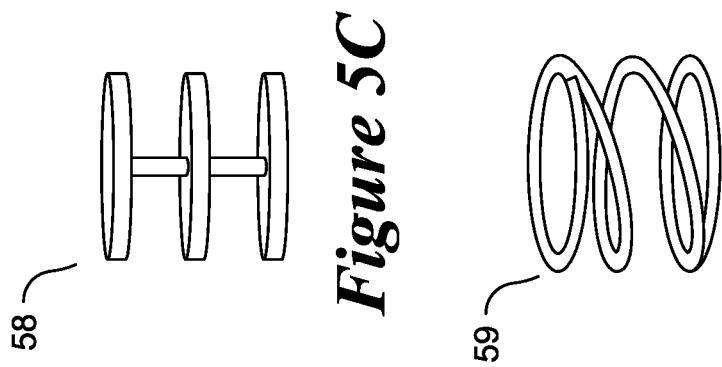
Figure 5C
Figure 5D
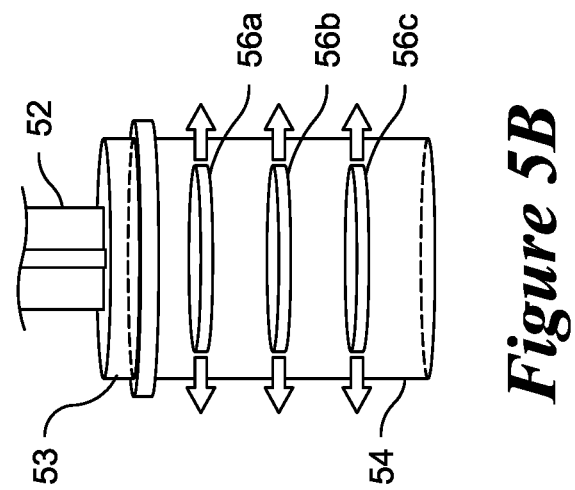
Figure 5B
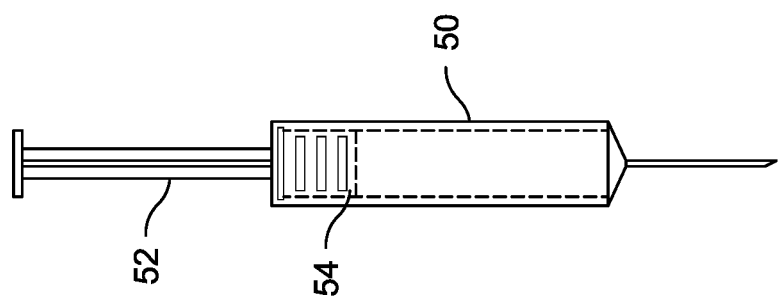
Figure 5A

CONTAINMENT AND DELIVERY SYSTEMS FOR CRYOGENIC STORAGE

CROSS-REFERENCE TO RELATED APPLICATIONS

This application is a National Stage of International Patent Application No. PCT/US2021/017065, filed Feb. 8, 2021, which claims the benefit of and priority to U.S. Provisional Patent App. No. 62/975,878, filed Feb. 13, 2020, the entire contents of which are hereby incorporated by reference in their entirety.

BACKGROUND OF THE INVENTION

Various embodiments of the present invention are directed to containment and delivery systems, and more specifically, containment and delivery systems that include elastomeric components configured to maintain a seal within a container at cryogenic temperatures.

In the selection of the packaging components for biologic and pharmaceutical materials, the integrity of the seal between the container and the closure is a consideration. These materials are typically stored in stoppered glass or plastic containers (e.g., glass or plastic vials or syringes) with an elastomeric closure. These materials include, for example, blood, serum, proteins, peptides, stem cells, DNA, and other perishable biological liquids, and freeze-dried or lyophilized drug products.

The container must be capable of protecting the materials from a variety of potential sources of contamination including microbial ingress, moisture and gas exchange. The primary seal is formed at the interface of the elastomeric seal component and the container. Assuming there are no defects in the individual packaging components, this interface represents the principal point of potential packaging failure. Multiple factors must be considered in the selection and application of the appropriate container closure system for a drug product to assure satisfactory container closure integrity.

Failures in manufacturing, such as improper assembly, inadequate or excessive crimping force, or faulty design can compromise the integrity of the container closure system. Therefore, it is imperative to ensure that the dimensions of the elastomeric seal component correctly match the container to establish adequate seal integrity. Vacuum loss, gas ingress and exchange, pH adjustments and contaminants can compromise seal integrity, which could lead to loss of sterility of the drug product that subsequently can affect product efficacy and increase the risk to patient safety.

With the increasing trend toward high-value biologics, cell and gene therapies, and other high-value drug products, the requirements for reliable container closure systems have become even more critical. Such biologics and drug products are typically sensitive to temperature, and the potential for degradation is significant if they are not stored under appropriate conditions. It is not uncommon for some biologics and drug products to be stored in sealed containers at temperatures as low as $0°$ C., more preferably $-80°$ C., and in many cases even lower at cryogenic temperatures (e.g., as low as or below $-150°$ C., more preferably as low as or below $-180°$ C., even more preferably as low as or below $-196°$ C.), for example to avoid degradation or evaporation loss of these materials.

As noted above, the sealing component of most drug containers is made of an elastomer. A common physical property of all elastomers is the glass transition temperature (Tg). All elastomers undergo a physical change at lower temperature where elastic properties are altered so that these materials are glass-like." Under ambient temperature conditions, the molecules are in a constant state of thermal motion and constantly change their configuration which provides flexibility and hence the ability to form a seal against another surface. However, at the glass transition temperature, the mobility of molecules is significantly reduced and the material becomes brittle and glass-like. For example, the glass transition temperature of common butyl rubbers is around $-65°$ C. Similarly, the coefficient of thermal expansion of the elastomeric material used to form the sealing component may substantially differ from the material of the container (e.g. glass or plastic), such that the elastomeric material contracts at a greater rate than the opening of the container. As used herein throughout the specification and the claims, "coefficient of thermal expansion" means volumetric thermal expansion coefficient. As a result, current elastomeric seal components may not be capable of maintaining closure integrity at cryogenic temperatures and could potentially compromise the sterility of the biologic or drug product stored in the container. Thus, there is a need for improved cryogenic containment and delivery systems and the components within those systems that provide the primary seal for ensuring container closure integrity.

BRIEF SUMMARY OF THE INVENTION

According to a first aspect of an embodiment of the present invention, a system for the containment or delivery of a product may comprise a container having an inner surface and a container closure having an outer surface. The container closure may comprise an elastomeric body and a material having a negative coefficient of thermal expansion within the elastomeric body. At least a portion of the container closure may be inserted within the container, such that at least a portion of the outer surface of the container closure contacts at least a portion of the inner surface of the container.

In some embodiments, the material having a negative coefficient of thermal expansion may comprise a solid, a liquid at a temperature greater than $0°$ C., or a gel at a temperature greater than $0°$ C. In other embodiments, the material may have a negative coefficient of thermal expansion at temperatures less than or equal to $0°$ C.

Moreover, some of the systems according to the various embodiments of the present invention may include a container closure provided in the form of at least one of a syringe plunger, vial stopper, and cartridge piston. In other systems, the container may be a vial having a neck portion and the system may further comprise a seal around an outer periphery of the container closure provided in the form of a vial stopper and at least a portion of the neck portion.

According to another aspect of an embodiment of the present invention, a system for the containment or delivery of a product may comprise a container having an inner surface, a container closure comprising an elastomeric body having an outer surface, at least a portion of the outer surface of the elastomeric body being in contact with the inner surface of the container, an insert at least partially embedded within the elastomeric body, an actuator having a distal end movably attached to the insert, and a resilient element between the distal end of the actuator and the insert. The resilient material may expand radially towards the inner surface of the container upon displacing the distal end of the actuator toward the insert.

In some embodiments, at least a portion of the resilient material is within the elastomeric body. In other embodiments, the resilient material comprises a material having a negative coefficient of thermal expansion. The material may be a liquid or a gel at a temperature greater than 0° C. The material may also have a negative coefficient of thermal expansion at temperatures less than or equal to 0° C.

According to yet another aspect of an embodiment of the present invention, a system for the containment or delivery of a product may comprise a vial having an inner surface and a neck portion, a stopper comprising an elastomeric body having an outer surface, an insert comprising a material having a negative coefficient of thermal expansion, and a seal around an outer periphery of the stopper and at least a portion of the neck portion. The insert may be located between a surface of the stopper and a surface of the seal.

In some embodiments, the material comprises a solid, a liquid or a gel at temperatures greater than 0° C. Furthermore, the material may have a negative coefficient of thermal expansion at temperatures less than or equal to 0° C.

These and other aspects of the present invention will be apparent in view of the following description.

BRIEF DESCRIPTION OF THE SEVERAL VIEWS OF THE DRAWINGS

Various aspects and embodiments of the application will be described with reference to the following figures. It should be appreciated that the figures are not necessarily drawn to scale. The figures depict one or more implementations in accord with the present concepts, by way of example only, not by way of limitations. In the figures, like reference numerals refer to the same or similar elements.

FIG. 5A is a front plan view of a system, and FIG. 5B is a magnified front perspective view of a container closure within the system of FIG. 5A according to a fifth embodiment of the present invention. FIGS. 5C and 5D are alternative embodiments of an insert that may be incorporated in the system of FIG. 5A.

DETAILED DESCRIPTION OF THE INVENTION

Generally, the systems according to the various embodiments of the present invention include a container closure comprising an elastomeric body and a material having a coefficient of thermal expansion that is less than the coefficient of thermal expansion of the elastomeric body. Preferably, the material has a negative coefficient of thermal expansion at a temperature less than or equal to 0° C., more preferably less than or equal to −80° C., and in many cases even lower at cryogenic temperatures less than or equal to −150° C., more preferably less than or equal to −180° C., and even more preferably less than or equal to −196° C. In some embodiments, the material may have a negative coefficient of thermal expansion at cryogenic temperatures (e.g. temperatures less than −150° C.). The material having a substantially different coefficient of thermal expansion assists in maintaining the seal within the system, thereby preventing the possible failure of container closure integrity and preserving the contents of the container when stored at low temperatures. Upon warming the system at ambient temperatures, the elastomeric portion of the container closure may expand to maintain the seal. The material having a low or negative coefficient of thermal expansion may be blended or combined with an elastomeric material used to form the body of the container closure. Alternatively, the container closure may have an elastomeric body that includes a chamber filled with the material. The chamber is preferably an internal chamber surrounded by the elastomeric body.

Figure 1:
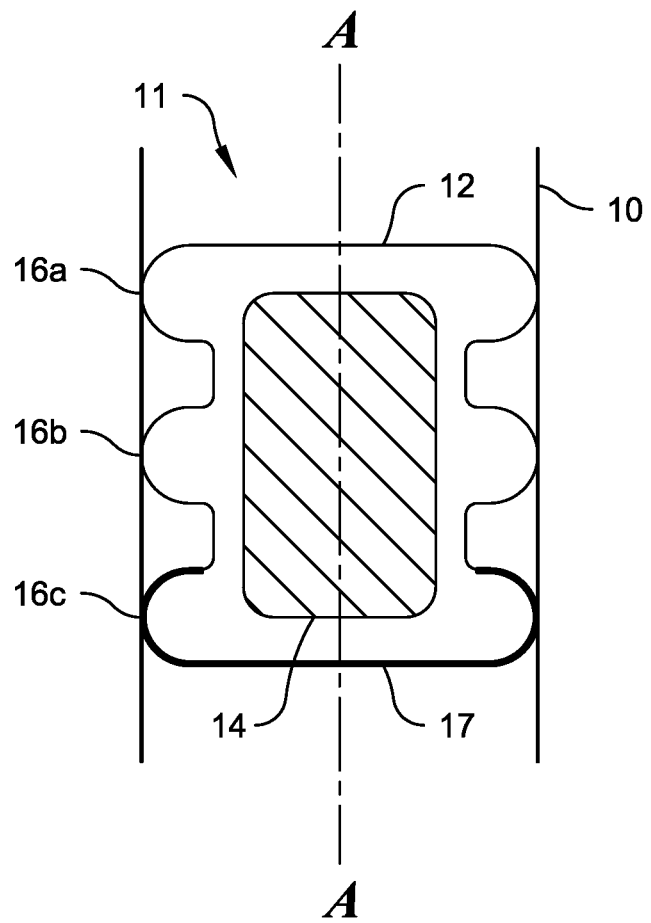
FIG. 1 is a schematic cross-sectional front plan partial view of a system according to a first embodiment of the present invention.

For example, referring to FIG. 1, a partial cross-sectional side view of a system according to a first embodiment of the present invention is provided. The system intended to hold the products for low temperature storage may be a sealed vial, cartridge, or syringe. The system includes a container 10 having an inner surface and a container closure 11 having an outer surface. The container closure 11 is at least partially inserted into the container 10, such that at least a portion of the outer surface of the container closure 11 contacts the inner surface of the container 10 and forms a seal against the inner surface of the container 10. The container closure 11 may comprise a plurality of materials. Preferably, the container closure 11 comprises at least a main body 12 made from an elastomeric material, and a second material 14 having a coefficient of thermal expansion that is less than the coefficient of thermal expansion of the elastomeric material.

The second material 14 is preferably located within the container closure 11 in a manner that will counter contraction of the elastomeric main body 12. For example, the system may have a centerline axis A-A, wherein the container closure 11 and container 10 are coaxial along the centerline axis A-A when assembled. When stored at low temperatures, such as cryogenic temperatures, the elastomeric material of the main body 12 may contract radially towards the centerline axis-A-A; however, the second material 14 having a lower coefficient of thermal expansion preferably contracts less, or more preferably, may expand radially away from centerline axis A-A if the coefficient of thermal expansion of the second material 14 is negative at the storage temperature. The amount of the second material 14 incorporated into the container closure 11 is dependent on the difference between the coefficients of thermal expansion of the second material 14 and elastomeric main body 12. For example, if the second material 14 has a coefficient of thermal expansion that is much less than the coefficient of thermal expansion of the elastomeric material, then less of the second material 14 may be required to attain the desired counter-action of the expected contraction of the elastomeric material. However, if the difference between the coefficients of thermal expansion between the two materials is small, a greater amount of the second material 14 may be required to achieve the same degree of resistance to the contraction of the elastomeric material.

The container closures of the systems according to the various embodiments of the present invention may be provided in the form of a syringe plunger, vial stopper, or cartridge piston, for example. Accordingly, the containers may be provided as a syringe, vial, or cartridge. As illustrated in FIG. 1, the container closure 11 may be provided in the form of a cartridge piston or syringe plunger having a plurality of ribs 16a, 16b, 16c that each extend radially in a plane that is generally perpendicular to the centerline axis A-A, wherein the outer circumference of at least one of the plurality of ribs 16a, 16b, 16c forms the seal with the inner surface of the container 10. The material 14 having a lower coefficient of thermal expansion is preferably located within the elastomeric main body 12 generally along the same plane as the one or more ribs 16a, 16b, 16c that provide the seal(s). In the embodiment of FIG. 1, the second material 14 occupies a single internal chamber within the elastomeric main body 12. In other embodiments, the second material 14 may occupy a plurality of internal chambers. For example, if the second material is immiscible in the elastomeric material, an emulsion or mixture of the materials may be formed before curing the elastomeric material, such that upon curing, the elastomeric material forms the continuous phase containing the second material in the form of the discontinuous phase. Alternatively, a system may be configured by providing the second material having a lower coefficient of thermal expansion outside of the main body of the container closure, which will be described in greater detail below.

The systems according to the various embodiments of the present invention may be used to contain and/or deliver pharmaceutical products. For container closures provided in the form of a syringe plunger or cartridge piston, the materials selected to prevent the overall contraction of the container closure at low temperatures, such as cryogenic temperatures, should not provide an excessive diametric interference at higher, ambient temperatures. For example, the force required to insert the syringe plunger or cartridge piston at the ambient temperatures at which the pharmaceutical product is filled in the container on a filling line or operate the syringe or cartridge when the product is administered manually by a medical professional should not exceed an acceptable limit. In other words, excessive force should not be required to actuate the container closures at ambient temperatures.

In order to limit or prevent potential interaction between the material having a lower coefficient of the thermal expansion with pharmaceutical products contained within the system, the outer surface of the container closure may be provided with an optional barrier layer, such as barrier layer 17 in FIG. 1. The barrier preferably covers at least a portion of the outer surface of the container closure that is most likely to contact any pharmaceutical products within the container of the system and prevents the leaching of the second material into the pharmaceutical product. As would be understood by those of skill in the art, the barrier is not limited to the embodiment illustrated in FIG. 1, but rather the optional barrier film may be applied to the surface of any of the embodiments of the present invention.

In a preferred embodiment, the barrier layer 17 is an inert film, preferably a fluoropolymer film. Fluoropolymers are readily known in the art and a detailed description of them is not necessary for a complete understanding of the present invention. Exemplary fluoropolymers include, but are not limited to, polytetrafluoroethylene (PTFE), ethylene tetrafluoroethylene (ETFE), homopolymers and copolymers of tetrafluoroethylene (TFE), perfluoroalkoxy polymer resin (PFA), copolymers of hexafluoropropylene and tetrafluoroethylene, polyethylenetetrafluoroethylene (PETFE), polyvinyl fluoride (PVF), fluorinated ethylenepropylene copolymers (FEP), polyethylenechlorotrifluoroethylene (PECTFE), polyvinylidene fluoride (PVDF), polychlorotrifluoroethylene, (PCTFE), and derivatives thereof. Preferably, the barrier layer 17 is formed of PTFE or ETFE.

Examples of the elastomeric material for forming the main body of the container closure according to the various embodiments of the present invention include, but are not limited to, polyisoprene; polybutadiene; styrene-butadiene copolymers; ethylene-propylene copolymers; ethylene-propylene-diene copolymers; chlorosulphonated polyethylene; ethylene-vinyl acetate copolymer; styrene-isoprene copolymers; fluoroelastomers such as FKM, perfluoro-elastomers (FFKM) and tetrafluoro ethylene/propylene rubbers (FEPM); synthetic or natural rubbers, such as butyl rubber, isoprene rubber, butadiene rubber, halogenated butyl rubber (e.g., bromobutyl rubber), ethylene propylene terpolymer, silicone rubber; combinations thereof and the like. Preferably, the elastomeric material is a butyl or halobutyl elastomer. The elastomeric material may further comprise one or more additives such as a vulcanizing agent, a vulcanizing accelerator, a vulcanizing activator, a processing aid, a filler, and a reinforcing agent to improve or enhance the properties of the elastomeric material.

As previously noted, the container included in the systems according to various embodiments of the present invention may be provided in the form of a syringe, vial, or cartridge, for example. Various common materials known by those of skill in the art may be used to form the containers. The materials may include, but are not limited to, polypropylene, COP, COC, glass, and combinations thereof. Other features of the system, if necessary, such as a plunger rod for actuating the syringe, may also be made from common materials known by those of skill in the art. The materials may include metallic or polymeric materials, including, but not limited to, stainless steel, aluminum, HDPE, LDPE, COP, COC, POM, nylon, polypropylene, and combinations thereof.

In some embodiments, the second material may be a liquid or gel having a desired freezing temperature that is selected based upon the expected storage temperatures of the system. Upon freezing, the second material should exhibit a coefficient of thermal expansion at the storage temperatures that will be less than the coefficient of the thermal expansion of the elastomeric material, more preferably a negative coefficient of thermal expansion. The liquid or gel may comprise one or more solvents and optionally contain one or more solutes, such that when combined, the liquid/gel has the desired freezing temperature and coefficient of thermal expansion. The one or more solvents may include, but are not limited to, water and aqueous mixtures. The one or more solutes may include, but are not limited to salt, sugar, glycerol, sorbitol, and combinations thereof, as well as other excipients that may alter the freezing properties of the solution. In other embodiments, the second material may include one or more solid materials, preferably a material having a negative coefficient of thermal expansion. The one or more solid materials may include, but are not limited to, alloys containing zirconium or hafnium and molybdenum or tungsten, titanium-based alloys (e.g. titanium alloys manufactured by ALLVAR), silicates (e.g. β-eucryptite, β-spodumenes and cordierite) graphene, and combinations thereof.

Referring again to FIG. 1, if the material having a low coefficient of thermal expansion is provided in the form of a liquid or gel, the elastomeric main body 12 may be molded to include an internal chamber that may be filled with the second material 14 by injecting the liquid into the chamber, for example. Any injections holes created to enable filling of the chamber may be closed after filling. Alternatively, the second material 14 may be an insert comprising either a solid material or a liquid material injected into a bladder or balloon that is then inserted or molded with the elastomeric material to form the container closure 11. In some embodiments, the container closure may include a plurality of chambers or inserts, such as the embodiment illustrated in FIGS. 5A and 5B in which a container closure 54 is attached to the distal end 53 of a plunger rod 52 and inserted into the barrel 50 of a syringe. The container closure 54 may be made of an elastomeric material and include a plurality of disc-shaped inserts or chambers 56a, 56b, 56c comprising a material having a negative coefficient of thermal expansion when the syringe is stored at low temperatures (e.g., cryogenic temperatures). In a preferred embodiment, the container closure may include a single chamber or insert, such as the insert 58 illustrated in FIG. 5C comprising a plurality of disc-shaped elements separated by spacers or the insert 59 in FIG. 5D in the shape of a spring having a plurality of coils. Using a single insert would reduce the number of molding steps necessary to form an elastomeric container closure containing a plurality of spaced expandable inserts.

Figure 6B:
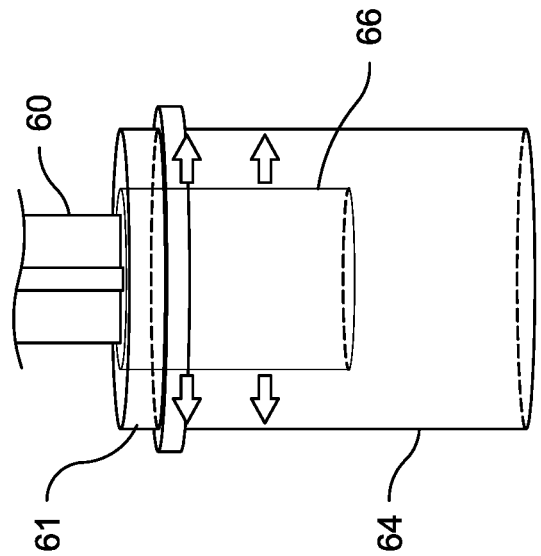
FIG. 6B is a magnified front perspective view of a container closure within the system of FIG. 6A according to a sixth embodiment of the present invention.
Figure 6A:
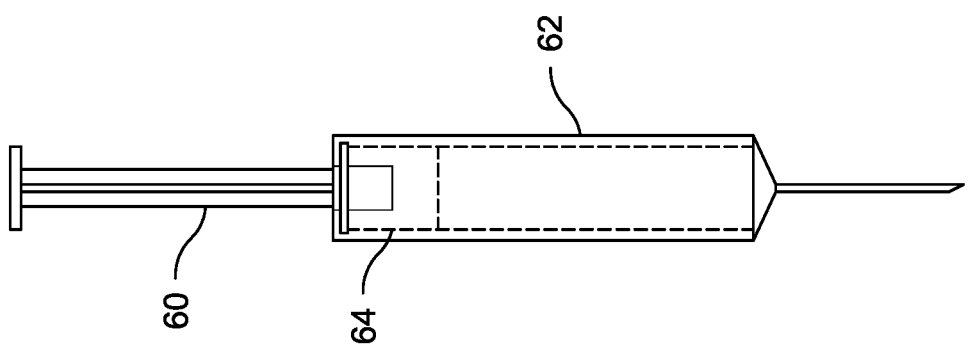
FIG. 6A is a front plan view of a system.
Figure 7B:
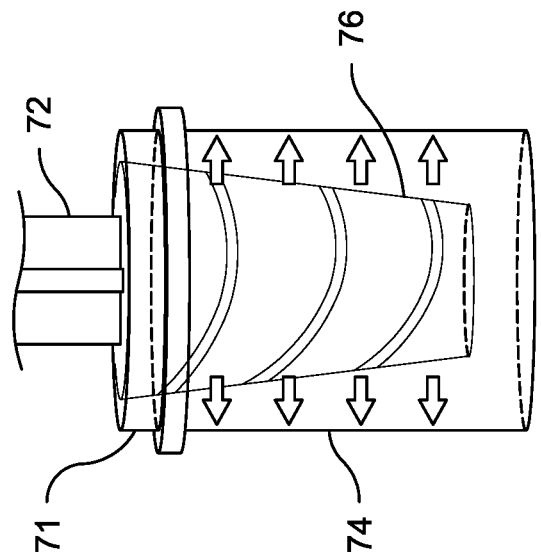
FIG. 7B is a magnified front perspective view of a container closure within the system of FIG. 7A according to a seventh embodiment of the present invention.
Figure 7A:
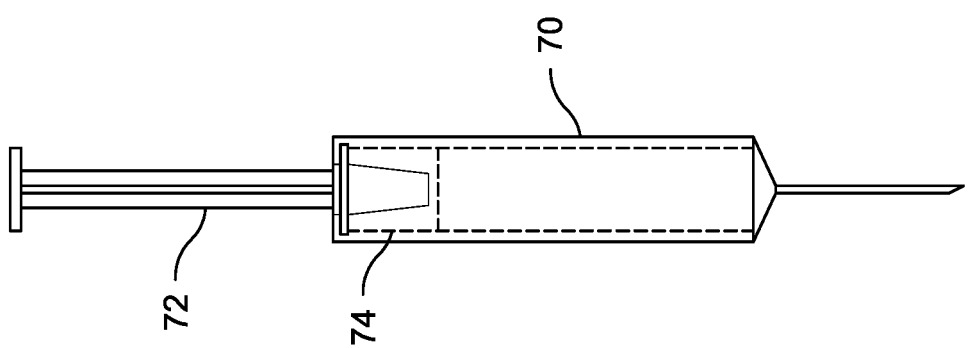
FIG. 7A is a front plan view of a system.

Similarly, the embodiments illustrated in FIGS. 6A to 7B also include container closures having a single expandable insert. In FIGS. 6A and 6B the container closure comprises an elastomeric outer sheath 64 that is formed over a single internal insert 66 comprising the material having a negative coefficient of thermal expansion. The insert 66 may be attached to the distal end 61 of the plunger rod 60 using various means known in the art, such as threading or an interference/snap fit. The embodiment of FIGS. 7A and 7B similarly includes an insert 76 comprising the material with a negative coefficient of thermal expansion, and the insert 76 may be fixedly attached to the distal end of the plunger rod 72. The insert 76 may further be provided with threads that allow the insert 76 to be coupled to an outer elastomeric sheath 74 having a corresponding threaded female receptacle for receiving the insert 76. The insert 76 is preferably screwed into the outer sheath 74 prior to low temperature storage to take advantage of the radial expansion of the insert 76 and promote a tight fit between the sheath 74 and the insert 76.

In some embodiments, the insert may be first inserted into a mold having the shape of the outer surface of the container closure, and the mold may then be filled by injection of the elastomeric material or with layers of elastomeric material into a compression mold, such that the insert is completely encapsulated with the elastomeric material. The insert is preferably made from a thermally stable material. However, to prevent thermal damage during the molding process to an insert provided in the form of a balloon or bladder, the container closure 11 may be partially cured and then subsequently, the container closure 11 may be post cured as necessary by a secondary process, such as oven post-cure, microwave curing, e-beam curing and the like. In order to provide a container closure including an insert at various depths, such as the embodiment illustrated in FIGS. 5A and 5B, the container closure may be molded in parts in several repeated steps. For example, in a first step, a first portion of the elastomeric component may be molded and partially cured with a cutout for the insert. A second portion of the elastomeric component could then be molded onto the first portion and then cured together with the insert in the middle of the two elastomeric portions of the component. This may be performed in a two-step or multiple step compression molding process, as known by those of skill in the art. Alternatively, a void could be left in a singular cured component and filled with a liquid or unpolymerized material. For systems in which the material having a negative coefficient of thermal expansion is located outside of the elastomeric component, the material may be provided in the form of a solid overlay that is mounted onto the elastomeric component.

Various methods of embedding a component into an elastomeric article are known in the art, such as the methods described in International Application Publication WO 2018/226780, the entire contents of which are incorporated by reference herein.

Figure 2A:
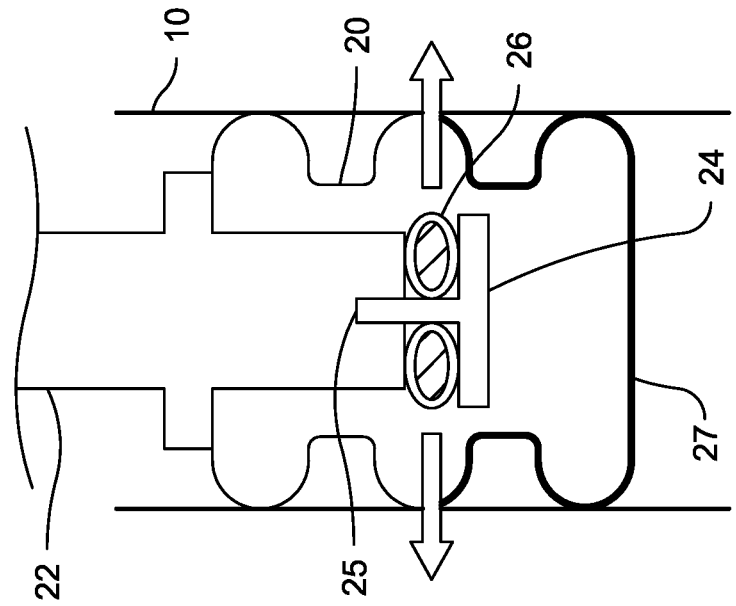
FIGS. 2A and 2B are schematic cross-sectional front plan partial views of a system according to a second embodiment of the present invention.

In an alternative embodiment, the systems for containment and/or delivery of products may be configured to include a structure that will allow for selective expansion of at least a portion of the container closure in the direction towards the sealing surfaces, i.e. radially outwards, thereby, providing a method to mechanically adjust the radial force of the sealing component against the inner surface of the container. This structure may be provided by a rigid component, such as a plunger rod for systems provided in the form of a syringe. For example, referring to FIGS. 2A and 2B, a partial cross-sectional side view of a second embodiment of the present invention is illustrated. The system comprises a container 10 having an internal surface and a container closure 20 in the form of a syringe piston, preferably made from an elastomeric material and having an outer surface, wherein at least a portion of the outer surface contacts and forms a seal with the inner surface of the container 10. The container closure 20 also has a product contact surface 27 at a first end and a bore in the opposing second end. Embedded within the container closure 20 is an insert 24 having a central pin 25 that axially extends into the bore of the container closure 20. A resilient material in the form of an expandable O-ring is located around the central pin 25. The O-ring may be made from the same or a similar elastomeric material as the container closure 20 or other resilient material. An actuator in the form of a plunger rod 22 may include a tip having a female receptacle that is configured to receive and connect to the central pin 25, preferably via threading. The bore of container closure 20 may similarly include threading that corresponds to threading around the outer circumferential surface of the side of the plunger rod 22. Upon coupling the distal end of the plunger rod 22 to the container closure 20 and insert 24, the O-ring 26 is compressed between the distal tip of the plunger rod 22 and annular surface around the central pin 25 of the insert 24, thereby providing rigid surfaces on either side of the O-ring 26. Compression of the O-ring 26 causes the O-ring 26 to expand radially towards the inner surface of the container 10, as represented by the arrows in FIG. 2B, thereby increasing the radial force of the seal between the container closure 20 and the inner surface of the container 10 in the plane of the O-ring 26, i.e. the plane that is perpendicular to the longitudinal axis of the container closure 20. If desired, the O-ring 26 may optionally include a material having a negative coefficient of thermal expansion to further promote expansion in the radial direction and sealing at low temperatures. Optionally, an inert film 27, as previously described, may be applied to at least a portion of the surface of the container closure that may potentially contact the contents of the container 10, such as the leading distal surface of the container closure 20 and up to the plane of the O-ring 26, for example. When the system is removed from cold storage and prepared for administration of the contents to a patient at ambient temperature, the plunger rod 22 may be unthreaded from the pin 25 in order to relax the resilient O-ring 26 and return the system to the original state illustrated in FIG. 2A. This will remove any excessive radial forces and ensure that the plunger rod 22 may be easily depressed to allow the container closure 20 to glide along the inner surface of the container 10.

Figure 2B:
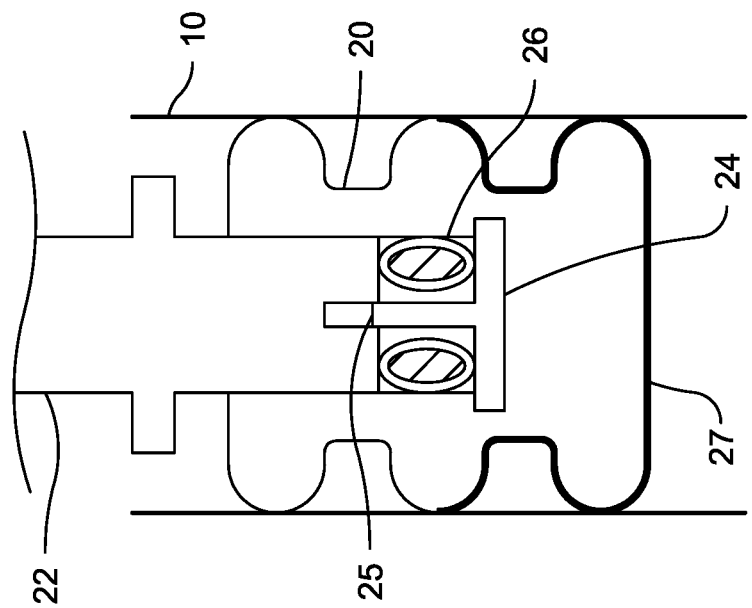
Figure 3A:
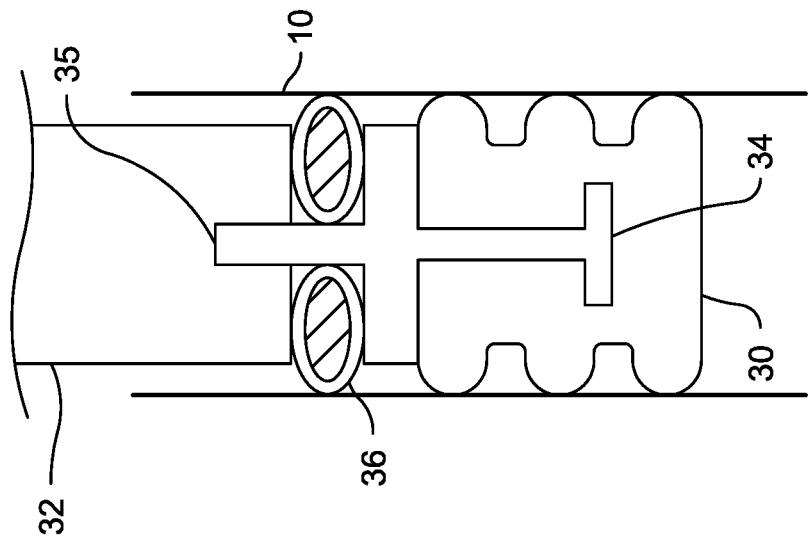
FIGS. 3A and 3B are schematic cross-sectional front plan partial views of a system according to a third embodiment of the present invention.
Figure 3B:
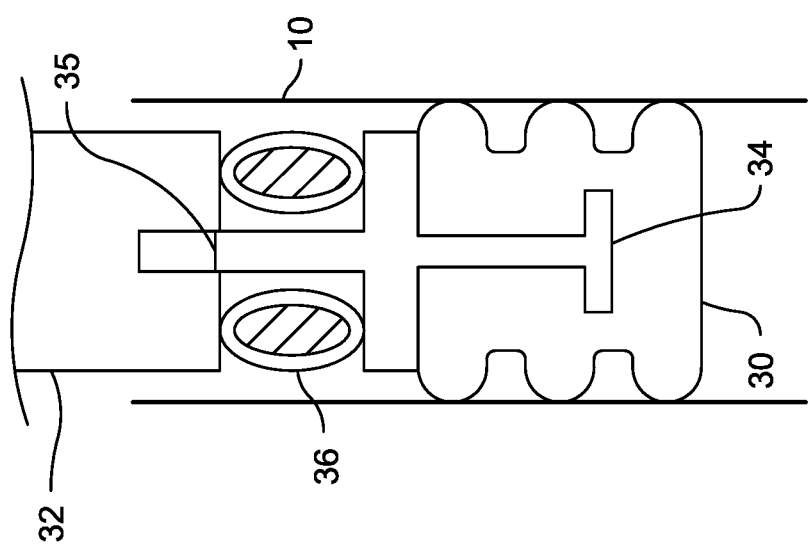

Another embodiment configured to allow for the selective mechanical adjustment of the radial force of a sealing component against the inner surface of the container is illustrated in FIGS. 3A and 3B. The embodiment of FIGS. 3A and 3B differs from the embodiment of FIGS. 2A and 2B in that the O-ring 36 is provided outside of the container closure 30. An insert 34 embedded in the container closure 30 may include a central axially extending pin 35, and the O-ring 36 is located on an annular surface surrounding the central pin 35; however, unlike the embodiment of FIGS. 2A and 2B, no portion of the central pin 35 or bladder 36 is located within the container closure 30. The distal tip of a plunger rod 32 may similarly include a female receptacle that may be coupled to the central pin 35, preferably via threading. Upon connecting the plunger rod 32 to the insert 34, the O-ring 36 is compressed between the distal tip of the plunger rod 32 and the annular surface around the central pin 35 causing the outer periphery of the O-ring 36 to contact the inner surface of the container 10 and form a seal. An increase in the compression of the O-ring 36 will proportionally increase the magnitude of the radial force of the outer periphery of the O-ring 36 against the inner surface of the container 10. The O-ring 36, similar the previous embodiment, may optionally contain a material having a negative coefficient of thermal expansion to further promote expansion in the radial direction and sealing at low temperatures. It is also preferred that the container closure 30, insert 34, and O-ring 36 may all be made from an inert material or at least be coated with an inert film because of the likelihood that the surface of these components will contact the contents of the container 10.

Figure 4A:
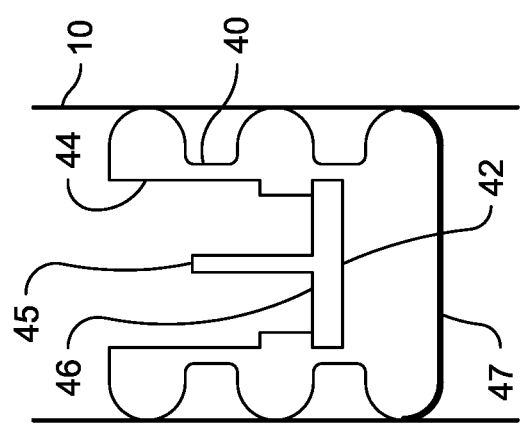
FIGS. 4A to 4C are schematic cross-sectional front plan partial views of a system according to a fourth embodiment of the present invention.
Figure 4B:
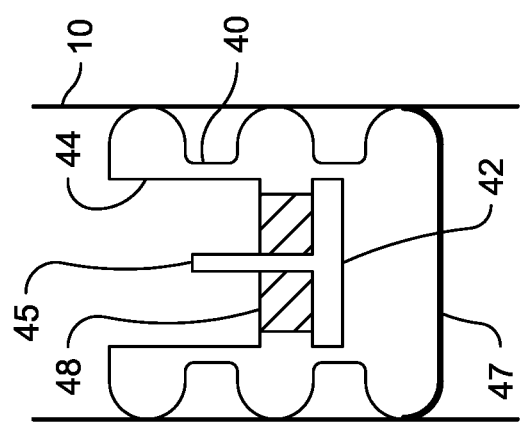
Figure 4C:
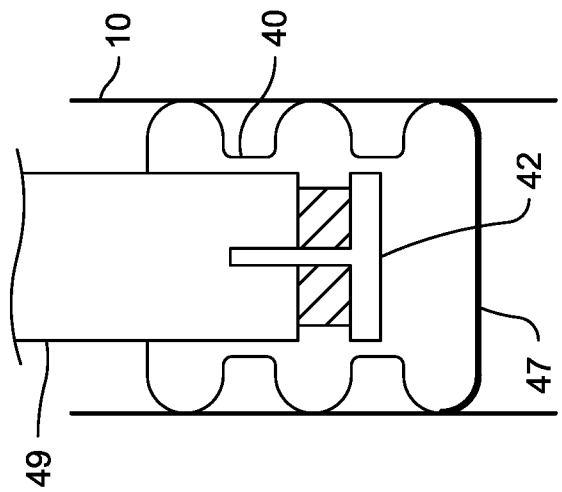

In yet another embodiment, a method of forming or assembling a system for containment and/or delivery of products is provided. For example, referring to FIGS. 4A to 4C, a container closure 40 may be molded to include an insert 42 embedded within the container closure 40 having an inert film on at least a portion of the surface of the container closure 40. Similar to the embodiment of FIGS. 2A and 2B, the insert 42 may have a central axially extending pin 45 that extends into a bore 44 located on the non-product contact side of the container closure 40. The bottom portion 46 of the bore 44 may be provided with a smaller diameter than the top portion of the bore 44 to create a well around the central pin 45. The container closure 40 may then be inserted into a container closure 10. In a subsequent step, as illustrated in FIG. 2B, the well may be filled with either an insert, such as the previously described compressible O-ring, or a material 48 having a negative coefficient of thermal expansion, such as an aqueous liquid, a gel, or a solid material, such as a metal disk or washer made of a material having a negative coefficient of thermal expansion. After filling the well with the material 48, a plunger rod 49 having a female receptacle in the distal tip may be connected to the central pin 45, preferably by threading, and seal the material 48 within the well. The outer circumference of the distal tip of the plunger rod 49 may also be provided with threads such that the plunger rod 49 may be attached to the top portion of the bore 44.

As would be appreciated by those of skill in the art, the embodiments illustrated in FIGS. 2A to 4C may be reconfigured, such that the central pin is provided on the distal tip of the plunger rod and the corresponding female receptacle provided within the insert.

As previously noted, the containment and delivery systems according to the various embodiments of the present invention may comprise a vial and vial stopper. For example, referring to FIGS. 8A and 8B, a container closure in the form of a vial stopper 81 may comprise an elastomeric main body 82 and a material 84 having a negative coefficient of thermal expansion. The material 84 may be a solid, liquid, or gel, for example. The material 84 may be located in an internal chamber filled with the material 84 (e.g. injecting a liquid material into an internal chamber of a molded stopper) or an insert comprising the material 84 may be overmolded to form the elastomeric main body 82, for example. The material 84 is preferably located within the portion of the stopper 81 below the flange 83 that will be inserted into the neck portion 85 of the vial 80. At low storage temperatures, such as cryogenic temperatures, the material 84 will expand to counteract any radial contraction of the elastomeric main body 82 and ensure a seal between the outer surface of the stopper 81 that is in contact with the inner surface of the neck portion 85 of the vial 80. Again, an optional inert film 87 may be applied to at least a portion of the outer surface of the stopper, most preferably the portion of the surface that is most likely to come into contact with the contents of the vial 80.

Figure 8A:
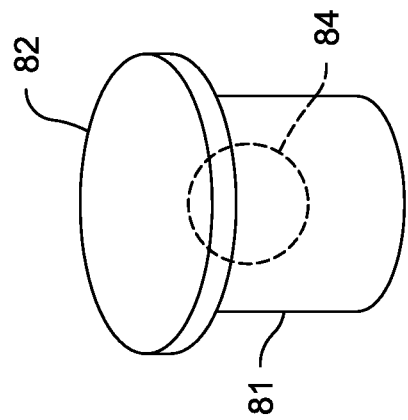
FIG. 8A is a schematic front perspective view of a container closure according to an eighth embodiment of the present invention.
Figure 8B:
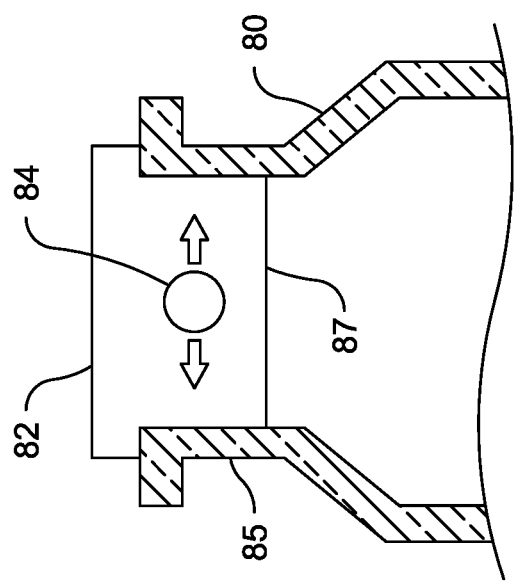
FIG. 8B is a schematic cross-sectional front plan partial view of a system containing the closure of FIG. 8A.
Figure 9A:
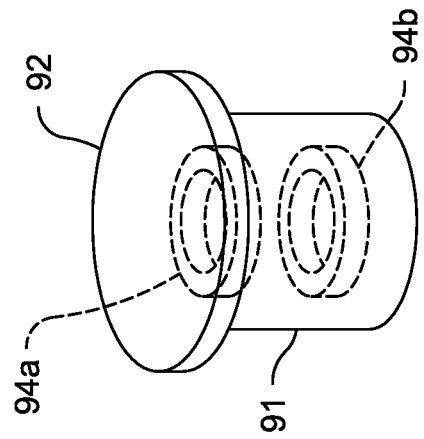
FIG. 9A is a schematic front perspective view of a container closure according to a ninth embodiment of the present invention and FIG. 9B is a schematic cross-sectional front plan partial view of a system containing the closure of FIG. 9A.
Figure 9B:
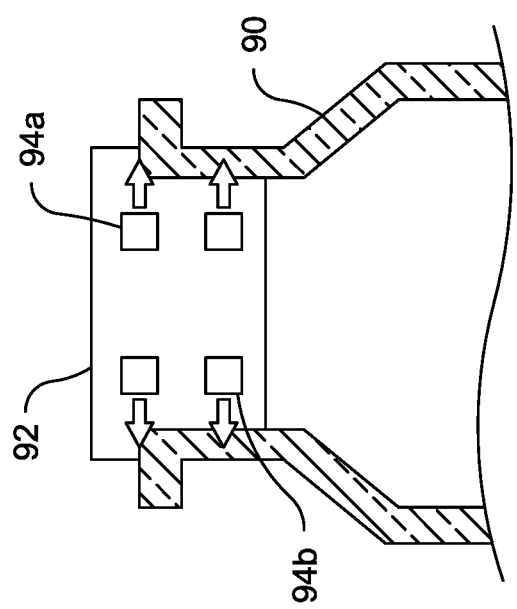
Figure 10A:
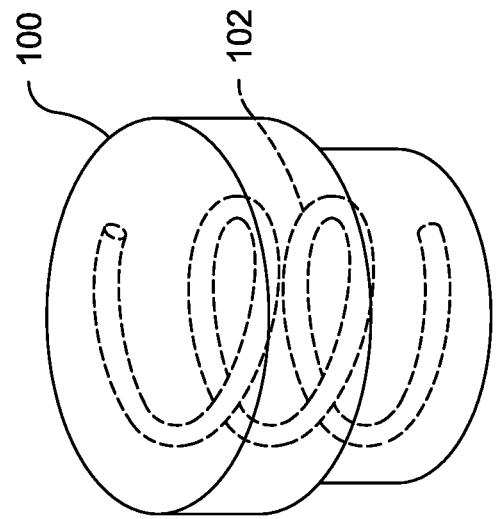
FIG. 10A is a schematic front perspective view of a container closure according to a tenth embodiment of the present invention and FIG. 10B is a cross-sectional front plan view of the container closure of FIG. 10A.
Figure 10B:
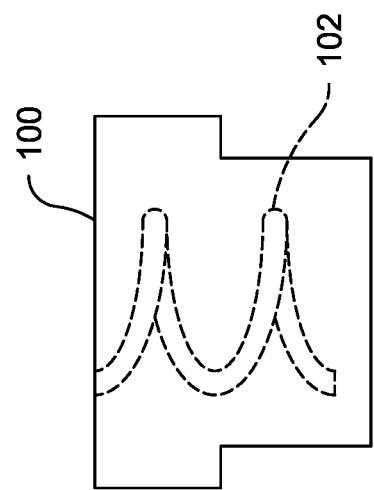

As illustrated in FIGS. 8A and 8B, the shape of the internal chamber or insert comprising the material 84 may be spherical, for example; however, the shape is not limited. Preferably, the internal chamber or bladder/insert may be tube-shaped, ring-shaped, coil-shaped or spiral shaped, such as the shape of the insert 94 or 102 in FIGS. 9A to 10B. These embodiments would all ensure that the radial sealing surface was maintained between the outer surface of the main portion of the of the container closure (81, 91, 100) that is in contact with the internal surface of the container (80, 90). By providing a shape with an internal through-hole, a syringe needle for puncturing the stopper and extracting the contents of the container may be inserted through the container closure without passing through the insert, thereby preventing potential exposure of the product within the container to the material having a negative coefficient of thermal expansion. As illustrated in FIGS. 9A and 9B, the material having a negative coefficient of thermal expansion may be provided in a plurality of ring-shaped inserts 94a, 94b rather than a single ring or tube-shaped insert.

The containment and delivery systems according to the various embodiments of the present invention may further comprise a seal configured to capture or retain the container closure within the container opening, such as the embodiments of FIGS. 11 to 14. These embodiments would all ensure that the axial sealing surface was maintained between bottom surface of the flange of the container closure and the top surfaces of the container. For example, referring to FIG. 11, a container closure in the form of a stopper 112 may be inserted into the opening and neck portion 110 of a vial. The stopper 112 may further include a flange portion 117 that rests on the top surface of the vial. A ring-shaped insert 114 comprising a material having a negative coefficient of thermal expansion may be located on the top surface of the stopper 112 above the flange portion 117. Finally, a seal, preferably a metal seal 116, such as an aluminum seal, may be crimped over the ring-shaped insert 114 and under the annular collar 115 of the vial. Crimping provides the seal 116 with an annular lip 118 that interferes with an annular collar 115 around the opening of the vial. The annular lip 118 abuts the underside of the annular collar 115 and assists in maintaining an axial force onto the top surface of the stopper 112. When the containment and delivery system is stored at low temperatures (e.g., cryogenic temperatures), the material 114 will expand in the axial direction to encourage or maintain the axial force applied to the top surface of the flange portion 117 of the stopper 112, which will contract at lower temperatures. Furthermore, the insert may be configured to promote axial instead of radial expansion of the material 114 having a negative coefficient of thermal expansion. For example, the ring-shaped insert may be a bladder having a rectangular cross-section, wherein the inner and outer circumferential walls of the ring, i.e. the vertical walls, are made from a rigid material, while the top and bottom walls of the ring, i.e. the horizontal walls, may be made from a more elastic material, such that expansion of a material inside the bladder will be primarily in the axial direction. In another example, a pair of concentric rings made of a rigid material may be configured and attached to a bottom surface of the seal, such that the ring-shaped insert may be inserted and nested between the concentric rings in an installed condition.

Figure 12:
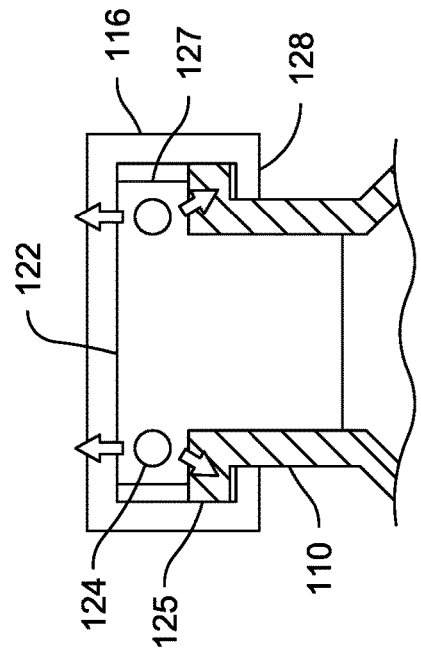
FIG. 12 is a schematic cross-sectional front plan partial view of a system according to a twelfth embodiment of the present invention.

In another embodiment, such as the embodiment of FIG. 12, a ring-shaped insert 124 comprising the material having a negative coefficient of thermal expansion may be located within the flange portion 127 of the stopper 122. The inner diameter of the ring-shaped insert 124 is preferably greater than the inner diameter of the neck portion 110 of the vial. As previously explained, axial expansion of the ring-shaped insert 124 against the crimped seal 116 will maintain close contact between the annular lip 128 of the seal 116 and the annular surface under the collar 125 around the opening of the vial, as well as force the flange portion 127 of the stopper 122 onto the top surface of the vial. To encourage axial expansion of the ring-shaped insert 124, an optional ring made of a rigid material may be applied around the outer circumferential surface of the flange portion 127 of the stopper 122.

Figure 13:
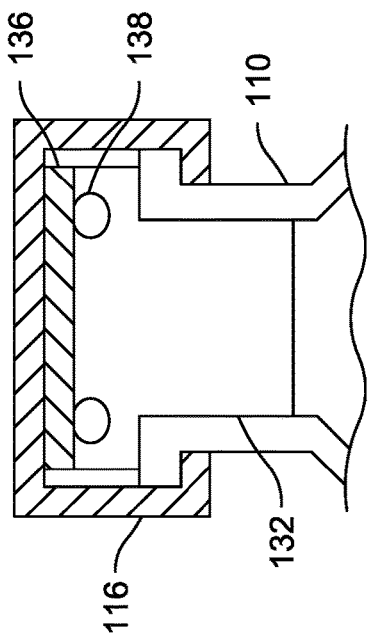
FIG. 13 is a schematic cross-sectional front plan partial view of a system according to a thirteenth embodiment of the present invention.

In yet another embodiment, such as the embodiment of FIG. 13, the top flange portion of the stopper 132 may be provided with a ring-shaped well 138. After the stopper 132 is inserted into the opening in the neck portion 110 of the vial, the material having a negative coefficient of thermal expansion, such as a solid, liquid or gel, may be inserted or injected into the well 138. A rigid cover 136 may be applied onto the top surface of the stopper 132 prior to crimping the seal 116 to seal the material in the well 138, as well as the stopper 132 in the neck portion 110 of the vial.

Figure 11:
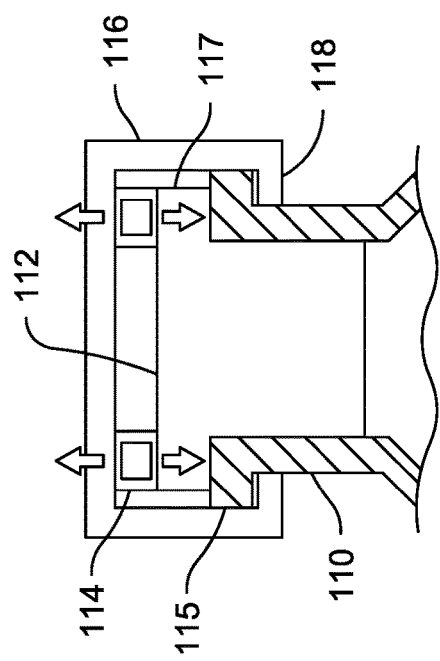
FIG. 11 is a schematic cross-sectional front plan partial view of a system according to an eleventh embodiment of the present invention.

In each of the systems described in FIGS. 11 to 13, the stopper may further optionally include a material having a negative coefficient of thermal expansion within the main body of the stopper, similar to the embodiments of FIGS. 8A to 10B, to also maintain the seal between the outer surface of the main portion of the stopper below the flange portion and the inner surface of the neck portion of the vial.

Figure 14:
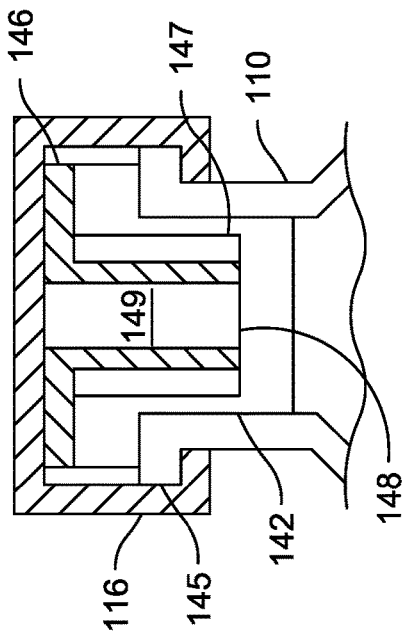
FIG. 14 is a schematic cross-sectional front plan partial view of a system according to a fourteenth embodiment of the present invention.

Referring now to FIG. 14, another containment and delivery system may include a stopper 142 having a bore 148 extending along the center axis of the main body of the stopper 142. A cover 146 made of a rigid material and having an axial projection that extends into the bore 148 may be used to seal a chamber between the outer surface of the axial projection and the inner surface of the bore 148. The axial projection of the cover 146 preferably includes an axially extending through-hole 149 to allow the needle of a syringe to be inserted through the stopper 142 and access the contents of a vial 110 that is sealed with the stopper 142. This chamber may be filled with the material 147 having a negative coefficient of thermal expansion. The system may further comprise a seal 116 that is crimped over the cover 146 and under the annular surface under the collar 145 around the opening of the vial 110, as previously described. When stored at low temperatures, the rigid cover 146 may encourage the outward radial expansion of the material 147 within the bore 148 to assist in maintaining a seal between the outer surface of the stopper 142 in contact with the inner surface of the neck portion of the vial 110. As would be appreciated by one of skill in the art, an additional ring-shaped well, such as well 138 in FIG. 13, may be incorporated into the flange portion of the stopper 142 of FIG. 14 that is filled with the same or similar material 147 having a negative coefficient of thermal expansion. In an alternative preferred embodiment of the present invention, the cover 146 may be made from a solid having a negative coefficient of thermal expansion (e.g. such as the alloys manufactured by ALLVAR of College Station, TX) that is over molded with an elastomeric material to form a stopper. In such an embodiment, the chamber may be eliminated. Again, similar to the embodiment of FIG. 8B, an optional inert film may be applied to at least a portion of the outer surface of any of the stoppers in the disclosed embodiments, most preferably the portion of the surface that is most likely to come into contact with the contents of the vial.

The components of the containment and delivery systems made according to the various embodiments of the present invention may be manufactured as previously described and bulk packaged into secondary packaging appropriate to maintain the sterility and cleanliness of the components. The components may then be sterilized by steam, EtOH, gamma irradiation or e-beam irradiation. The sterile bulk packaged product may then be introduced into the aseptic filling environments, for example.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A system for containment or delivery of a product, the system comprising:
    a container having an inner surface; and
    a container closure configured to at least partially be received in the container to close the container, the container closure comprising an elastomeric body and a material having a negative coefficient of thermal expansion, the material being disposed within an outer surface of the elastomeric body,
    wherein at least a portion of the outer surface of the elastomeric body contacts at least a portion of the inner surface of the container, and the material defines an internal through-hole configured to receive a needle puncturing the elastomeric body.

2. The system of claim 1, wherein the material comprises a solid.

3. The system of claim 1, wherein the material comprises a liquid at a temperature greater than 0° C.

4. The system of claim 1, wherein the material comprises a gel at a temperature greater than 0° C.

5. The system of claim 1, wherein the material has the negative coefficient of thermal expansion at temperatures less than or equal to 0° C.

6. The system of claim 1, wherein the container closure is a vial stopper.

7. The system of claim 6, wherein the container is a vial having a neck portion, and the system further comprises a seal around an outer periphery of the vial stopper and at least a portion of the neck portion.

8. The system of claim 1, wherein the material has a shape of a tube, a ring, a coil, or a spiral.

9. The system of claim 1, wherein the container closure includes a second material having a negative coefficient of thermal expansion within the elastomeric body spaced apart from the material.

10. A system for containment or delivery of a product, the system comprising:
    a container having an inner surface;
    a container closure comprising an elastomeric body having an outer surface, at least a portion of the outer surface of the elastomeric body configured to be in contact with the inner surface of the container;
    an insert at least partially embedded within the elastomeric body;
    an actuator having a distal end movably attached to the insert; and
    a resilient element between the distal end of the actuator and the insert,
    wherein the resilient element expands radially towards the inner surface of the container upon displacement of the distal end of the actuator toward the insert, and the resilient element comprises a material having a negative coefficient of thermal expansion.

11. The system of claim 10, wherein at least a portion of the resilient element is within the elastomeric body.

12. The system of claim 10, wherein the material having the negative coefficient of thermal expansion comprises a liquid at a temperature greater than 0° C.

13. The system of claim 10, wherein the material having the negative coefficient of thermal expansion comprises a gel at a temperature greater than 0° C.

14. The system of claim 10, wherein the material has the negative coefficient of thermal expansion at temperatures less than or equal to 0° C.

15. A system for containment or delivery of a product, the system comprising:
    a vial having an inner surface and a neck portion;
    a stopper comprising an elastomeric body having an outer surface;
    an insert comprising a material having a negative coefficient of thermal expansion; and
    a seal around an outer periphery of the stopper and at least a portion of the neck portion,
    wherein the insert is located between a surface of the stopper and a surface of the seal.

16. The system of claim 15, wherein the material comprises a solid.

17. The system of claim 15, wherein the material comprises a liquid at a temperature greater than 0° C.

18. The system of claim 15, wherein the material comprises a gel at a temperature greater than 0° C.

19. The system of claim 15, wherein the material has the negative coefficient of thermal expansion at temperatures less than or equal to 0° C.

20. A system for containment or delivery of a product, the system comprising:
    a container having an inner surface; and
    a container closure configured to at least partially be received in the container to close the container, the container closure has a plurality of ribs that each extend radially in a plane that is perpendicular to a centerline axis of the container closure and contact at least a portion of the inner surface of the container, the container closure comprising an elastomeric body and a material having a negative coefficient of thermal expansion, the material being disposed within the elastomeric body in the same plane as one or more of the plurality of ribs.

21. The system of claim 20, wherein the container is a syringe, and the container closure is a plunger.

22. The system of claim 20, wherein the material has the negative coefficient of thermal expansion at temperatures less than or equal to 0° C.

* * * * *